United States Patent
Malinow et al.

(10) Patent No.: US 6,960,470 B1
(45) Date of Patent: Nov. 1, 2005

(54) DIAGNOSTIC METHODS FOR DRUG SCREENING FOR ALZHEIMER'S DISEASE

(75) Inventors: Roberto Malinow, Cold Sprg Hrb, NY (US); Shahid Zaman, Cold Spring Harbor, NY (US); Sangram S. Sisodia, Chicago, IL (US); David R. Borchelt, Baltimore, MD (US); Michael K. Lee, Baltimore, MD (US)

(73) Assignee: Cold Spring Harbor Laboratory, Cold Spring Harbor, NY (US)

( * ) Notice: Subject to any disclaimer, the term of this patent is extended or adjusted under 35 U.S.C. 154(b) by 0 days.

(21) Appl. No.: 09/353,126

(22) Filed: Jul. 14, 1999

Related U.S. Application Data

(63) Continuation of application No. 09/193,221, filed on Nov. 16, 1998, now abandoned.

(51) Int. Cl.[7] .............................. C12N 5/02; C12N 5/06
(52) U.S. Cl. ........................ 435/325; 435/352; 435/354
(58) Field of Search ................................ 435/325, 352, 435/354, 1.1, 320.1, 440; 424/93.1, 277.1

(56) References Cited

PUBLICATIONS

Skolnick et al., Trends in Biotech 18(1):34–39, 2000.*
Kandel et al., Principles of Neural Science, Elsevier, 3rd Ed., 1991:206–209 and 1019–23.*
Crooke et al., Nature Medicine Apr. 1998 4(4):452–5.*
Voet & Voet (1995) "Biochemistry (2nd Ed.): Chapter 15 Introduction to Metabolism" (pp. 412–442).*
Allsop et al. "Modulation of b-amyloid production and fibrillization." Biochem. Soc. Symp. 67: 1–14.*
Lodash et al. (1997) "Molecular Cell Biology: Chapter 8 'Genetic Analysis in Cell Biology'" (pp. 263–303).*
Bradford (1986) "Chemical Neurobiology An Introduction to Neurochemistry Two Inhibitory Amino Acids: GABA and Glycine." (pp. 229–242).*
Ikeda et al. (Dec. 1996) "The Clinical Phenotype of Two Missense Mutations in the Presenilin I Gene in Japanese Patients." Ann. Neurol. 40(6): 912–917.*
Skolnick & Fetrow (2000) "From genes to protein structure and function: novel applications of computational approaches in the genomic era." Trends in Biotech. 18(1): 34–39.*
Jobling & Holmes (1991) "Analysis of structure and function of the B Subunit of cholera toxin by the use of site–directed mutagenesis." Molecular Microbiology 5(7): 1755–67.*
Hevers & Luddens (Aug. 1998) "The diversity of GABAA receptors. Pharmacological and electrophysiological properties of GABAA channel subtypes." Mol. Neurobiol. 18(1): 35–86.*
Smith, Elements of Molec. Neurobiol., 2nd Ed., 74–82 and 460–70, 1996.*
Parent et al., Neurobiology of Disease 6:56–62, Jun. 17, 1999.*
Bliss et al. (1993) Nature 361:31–39.
Borchelt et al. (1996) Neuron 17: 1005–1013.
Evans, et al. (1996) Neuropharmacology 35: 347–357.
Fastbom et al. (1998) Alzheimer Dis Assoc. Disord. 12: 14–17.
Guo et al. (1996) Neuroreport. 8: 379–383.
Muir et al. (1996) J. Cereb. Blood Flow Metab. (16): 1211–1218.
Ohkuma et al. (1994) Jpn. J. Pharmacol 64:125–128.
Shen, et al. (1997) Cell 89: 629–639.
Wigstrom et al. (1986) J. Physiol. (Paris) 81: 228–236.
Wong et al. (1997) Nature 387: 288–292.
Borchelt et al. (1997) Neuron 19:939–45.
Darnell et al. (1986) Molec. Cell Biology pp. 400–401.
Davis et al. (1998) Neuron 20:603–09.
Lee et al. (1997) Nat. Med. 3:756–60.
Naruse et al. (1998) Neuron 21:1213–21.
Parent et al. (1999) Neurobiology of Disease 6:56–62.
Smith (1996) Elements of Molec. Neurobiology, $2^{nd}$ Ed, pp. 74–82 and 460–470.

* cited by examiner

Primary Examiner—Brenda Brumback
Assistant Examiner—Christopher James Nichols
(74) Attorney, Agent, or Firm—Barbara Rae-Venter; Rae-Venter Law Group

(57) ABSTRACT

Methods of screening candidate drugs for the treatment of Alzheimer's disease are provided. Employing tissue slices of mutant mouse hippocampal cells having an extra copy of a mutant form of the presenilin-1 gene, it is found that these cells have enhanced potentiation to tetanic stimuli. By subjecting both wild-type and mutant hippocampal cells to tetanic stimuli in the presence of a candidate drug, reduction of the enhanced potentiation of the mutant cells without significant change in the potentiation of the wild-type cells indicates a successful candidate.

8 Claims, No Drawings

DIAGNOSTIC METHODS FOR DRUG SCREENING FOR ALZHEIMER'S DISEASE

This is a continuation of prior application Ser. No. 09/193,221 filed on Nov. 16, 1998, now abandoned.

TECHNICAL FIELD

The field of this invention is the screwing of drugs for treatment of Alzheimer's and related neurodegenerative diseases.

BACKGROUND

Alzheimer's disease (AD) is the most common cause of dementia in the elderly. Mutations in the amyloid precursor protein gene (APP) and presenilins (1 and 2; PS1 and PS2) cause autosomal dominant, early-onset forms of AD and account for ~1% and ~50% of inherited cases, respectively. Polymorphisms in the apoE4 and α-2 macroglobulin genes are associated with increased risk in individuals over 60 years of age.

The presenilins are polytopic membrane proteins expressed in the endoplasmic reticulum, Golgi complex in dendrites (close to dendritic spines) and axon terminals in neurons. The PS1 holoprotein is subject to endoproteolysis; the resulting N- and C-terminus fragments bind to each other at stoichiometric levels and/or other proteins, such as γ-catenin. The levels of the fragments are very tightly regulated and overexpression studies show little changes in the relative amounts of accumulated fragments.

The normal biological function(s) of presenilins are not well understood although they have been shown to play a major role in the embryonic development of the axial skeleton and cerebral vasculature. The inheritance pattern in humans carrying mutant presenilin genes suggests a gain-of-function. Several cellular effects of mutant presenilins have been documented that may be relevant to the pathophysiology of AD. First, in cultured cells and transgenic animals expression of mutant presenilins lead to the elevated production of αβ42(43) peptides that are deposited early and selectively in amyloid plaques in AD. The over-production of Aβ42(43) is most pronounced in cells expressing a PS-1 mutation lacking exon 9 (Δ9). Secondly, cells expressing mutant presenilins also have aberrant calcium homeostasis; PC12 cells expressing mutant PS1 stimulated with agonists that activate $Ca^{2+}$ efflux from intracellular stores, exhibit larger calcium transients than cells expressing wild-type (wt) PS1.

The clinical hallmark of early AD is a disruption of memory processes. The hippocampus, which is prominently involved in the formation of memory, is affected early in the disease and shows the characteristic histopathological changes of AD, namely senile (amyloid) plaques and neurofibrillary tangles. A loss of synapses is also apparent in the hippocampus early in the disease. As the disease progresses, neuronal death in the hippocampus increases (see review by Price et al., 1998 Annu. Rev. Neurosci. 21:479–505).

Hippocampal slices have been effectively used to examine synaptic transmission and plasticity in vitro. Stimulation of CA1 *striatum radiatum* afferent pathways produces a mixed excitatory and inhibitory synaptic response in pyramidal neurons. Brief repetitive stimulation generates a short and long-term potentiation (STP: ~20 min and LTP: >30 min) of excitatory transmission that have been proposed as cellular correlates of some forms of leaning. STP and LTP also share several underlying mechanisms with glutamate-mediated neuron death (excitotoxicity, see reviews by Obrenovitch et al., 1997 J. Prog. Neurobiol. 51:39–87 and Choi, 1992 J. Neurobiol. 9:1261–1276). All are believed to require synaptically induced postsynaptic depolarization, activation of NMDA receptors and a rise in intracellular calcium concentration. As membrane depolarization is a critical requirement for STP and LTP, these phenomena are sensitive to pharmacological manipulations of fast inhibitory pathways via the $GABA_A$ receptor. In the CA1 region of the hippocampus, for example, a $GABA_A$ antagonist leads to more LTP, while $GABA_A$-potentiating benzodiazepines can reduce LTP. $GABA_A$ agonists can also decrease glutamate-induced excitotoxicity.

Based on the present understanding of the etiology of AD and the neuronal mechanisms associated with AD and memory, there is a need for a diagnostic method for evaluating the potential of drugs for the treatment of AD, both prophylactically and therapeutically.

BRIEF DESCRIPTION OF RELEVANT ART

The effect of benzodiazepines in decreasing the incidence of AD has been described by Fastbom et al., 1998 Alheimer Dis. Assoc. Disord. 12:14–17. Mechanisms associated with learning, excitatory transmission and the involvement of $GABA_A$ receptor are described by Bliss et al., 1993 Nature 361:31–39; Wigstrom et al., 1986 J. Physiol. (Paris) 81:228–236; Evans, et al., 1996 Neuropharmacology 35:347–357; Ohkuma et al. 1994 Jpn. J. Pharmacol. 64:125–128; and Muir et al., 1996 J. Cereb. Blood Flow Metab. 16:1211–1218. Biological functions and cellular effects of presenilins are described in Shen et al., 1997 Cell 89:629–639; Wong et al., 1997 Nature 387:288–292; Lee et al., 1997 Nat. Med. 3:756–760; and Borchelt et al., 1996 Neuron 17:1005–1013. Guo et al., 1996 Neuroreport. 8:379–383 report that cells having mutant presenilins have aberrant calcium homeostasis.

SUMMARY OF THE INVENTION

Mutant presenilin comprising hippocampal cells are employed in an assay for screening drugs for the treatment of Alzheimer's disease. Tissue samples from the hippocampus having a presenilin mutation are subjected to tetanic stimulation in the presence of a candidate drug and cellular plasticity is determined, as compared to the presence of a control. The measured outcome is reduction of aberrant signaling.

DESCRIPTION OF RESULTS

A study of basal transmission and paired-pulse facilitation (PPF) was graphed to provide examples of field responses in hippocampal slice CA1 region evoked by delivery of increasing intensity stimuli for wild-type ("wt") and Δ9 mutant animals (averages of 5 each). is A graph was made of the input-output plot of basal transmission in mutant and wt animals obtained from responses evoked as above. The plot includes data from 4 wt and 6 mutant slices. Best fit line to each group (linear regression) shows slopes that are not significantly different (p>0.05). A graph was made which shows examples of responses to paired stimuli (50 ms inter-stimulus interval, averages of 10 each). A graph was made which is a plot of percent potentiation versus inter-pulse interval for mutant (Δ, n=6 slices) and wt (O, n=6 slices) animals. Values and not significantly different (p>0.05).

Graphs were made of epsp response to tetani in the presence or absence of agents which affect the role of $GABA_A$ receptor to evaluate the role of $GABA_A$ in the presence or absence of agents, which affect the $GABA_A$ receptor. Data are based on experiments with $GABA_A$ transmission intact. Data include examples of epsp response (averages of 10 each) immediately before and 20 min after a tetanus superimposed for wt and mutant animals. The graphs include a plot of mean epsp slope (±SEM) normalized to values before tetanic stimulus (time 0). For each slice transmission two independent pathways were monitored. Tetanized pathway showed greater enhancement in slices from mutant (n=8 slices) than wt (n=10 slices) animals. Control pathways (mutant and wt) remained unchanged. Tetanus consisted of 100 stimuli delivered over 1 sec (100 Hz). The potentiation at the time points of 5, 10, 15, 20, 25 and 30 min was: 1.36±0.060, 1.26±0.058, 1.27±0.054, 1.24±0.058, 1.22±0.063 and 1.21±0.069, respectively for the wt. For the same time points for the mutant these values were: 1.67±0.065, 1.52±0.054, 1.54±0.072, 1.56±0.075, 1.51±0.089 and 1.54±0.090, respectively. At these time points, there was a statistically significant difference between the two sets of data points ($<0.05$). A graph was made which shows results with $GABA_A$ transmission blocked with 100 $\mu M$ picrotoxin. Data are examples of epsp responses (average of 10 each) immediately before and 20 min after a tetanus superimposed for wt and mutant animals. Data are a plot of mean epsp slope±SEM normalized to values before tetanic stimulus (time 0). For these experiments, control pathways were monitored for only 30 min after tetanus. Tetanized pathways showed similar enhancement in slices from mutant (n=13 slices) and wt (n=18 slices) animals. Control pathways (mutant and wt) remain unchanged. Tetanus consisted of 25 pulses given as groups of 5 pulses at 100 Hz every 10 s, 5 times. This tetanus was weaker than above to obviate possible differences between wt and mutant induction. Data were developed and graphed which showed the results of experiments in the presence of N-methyl-D-aspartate (NMDA)-receptor blockade with AP5. Plot of mean epsp slope±SEM normalized to values before tetanic stimulus (time 0).

Data were developed and graphed which showed the effect of flunitrazepam on LTP. Data were prepared as a graph of the means±SEM of normalized epsp responses in the absence of drug plotted against time: wt (n=7 slices), and $\Delta 9$ mutation (n=12 slices). There was a significantly greater amount of potentiation in the mutant at the time points of 5, 10 and 15 min post-tetanus. At 20 min, the difference in potentiation became insignificant. The tetanus (delivered at time 0) was 100 pulses given for 1 s (100 Hz) every 20 s 3x in succession. Control pathways (receiving no tetanus) remain unchanged. In the presence of flunitrazepam in the bathing medium; (n=11 slices) and $\Delta 9$ mutation (n=8 slices) there was no statistically significant difference between the two groups at the above time points post-tetanus. Control pathways (receiving no tetanus) remained unchanged. Comparing potentiation in mutants (+FLU) with the wt (−FLU) shows the suppression of the each the potentiation to almost the wt levels. Histograms were prepared from the data of the following paragraph and showed potentiation at various times post-tetanus. All groups were compared with each other, and the statistical significance of the different pairs ($p<0.05$) determined. These comparisons were calculated for 5 min, 10 min (histogram not shown) and 15 min. These time points gave identical statistical results for pairwise comparisons as in the 5 min case. For the 20 min time point, however, the W vs. M comparison was not significant but the other two pairwise group comparisons were significant at ($p<0.05$).

Data were prepared as graphs of the effect of agents on the $GABA_A$ receptor-mediated transmission in the mutant and wt cells using whole-cell patch-clamping. The data included the evoked synaptic response (averaged up to 20 each) from whole-cell patch-clamped neurons. Outward current recorded at 0 mV is completely blocked by 100 $\mu M$ PTX, a $GABA_A$ receptor antagonist. NBQX blocked some of the outward current (not shown) indicating some di-synaptic inhibition. At the holding potential of −60 mV, the inwood current is completely blocked with 2 $\mu M$ NBQX, the AMPA (glutamate subtype) receptor blockade. The evoked synaptic responses (averaged up to 15 each) recorded at holding potentials of 0 mV and −60 mV with the stimulating electrode placed in stratum radiatum at site 1, ~50$\mu m$ from the recording electrode at site 2, ~250 $\mu m$ from the recording electrode and at site two with the stimulus intensity increased ~3-fold. Graphs were prepared of examples of averaged (up to 15 each) traces from patch-clamp whole-cell recordings-in wt and $\Delta 9$ mutation at −0.60 mV (glutamate currents) and at 0 mV ($GABA_A$ currents). The graphs included peak amplitude of response ratios (measured at holding potentials of −60 mV and 0 mV, respectively) from cells in individual slices (n=9 slices each). The ratios a significantly greater in the mutant than in the wt ($p<0.05$, t-test).

Also graphed were the results from the effects of AP5-sensitive potentials during tetanus. One of the graphs show's normalized traces of field potential response to four consecutive (every 10 ms) stimuli, before (the larger response) and after (the intermediate response) the application of the specific NMDA-receptor antagonist, AP5. The responses were normalized to the area up to the peak of the first response (which is mostly due to non-NMDA receptor activation Another graph shows the averaged differences of areas under the four response curves, before and after AP5 application in individual (wt and $\Delta 9$ mutant) slices to show the effect of tetanus on the NMDA (or AP5)-sensitive component. Although the mean AP5-sensitive potentials were smaller in the mutants (despite manifesting a greater potentiation), there was no statistically significant difference between the two groups.

DETAILED DESCRIPTION OF THE INVENTION

A method for screening drugs is provided for determining their potential for the treatment of Alzheimer's disease (AD). The effect of agents on changes in plasticity of mutant cells is related to their ability to treat AD. It is found that cells with presenilin mutations, particularly PS-1, can be used in a battery of tests to evaluate plasticity of cells to tetani, where restoring wild-type behavior indicates potential use as a therapeutic.

Mammalian species may be used as a source of mutant hippocampal tissue. Any mutant which provides the desired enhanced synaptic potentiation upon tetanic stimuli in the same manner as observed with a PS-1 mutation may be employed. This can be achieved in a variety of ways of varying convenience. A transgenic mammalian host can be employed where a mutated presenilin gene is introduced, where it acts as an autosomal dominant allele. Alternatively, one may provide a transgenic host, where presenilin antisense is transcribed from an inducible promoter. Also, one can infect cells or tissue with viruses which provide such genetic capability as described above. In some situations, transformed or otherwise immortalized hippocampal cells may be employed for genetic modification. Other techniques may also be used to provide the desired mutant. The mutation is in a presenilin gene, particularly PS-1. While any mammal may be used as the source of the tissue, for convenience murine species, rats and mice, may be employed, although primates other than humans, or domestic animals, such as porcine, feline, canine, lagomorpha, etc. may also find use. Lee et al., 1997 Nat. Med. 3:756–760, describes hyperaccumulation of FAD-linked presenilin variants in vivo.

In carrying the assay out, there may be an interest in first determining synaptic transmission and plasticity in hippocampal slices of wild-type and mutant hosts. Synaptic transmission is elicited by delivering stimuli of different intensities to afferent pathways. Input-output curves are generated by plotting the slopes of excitatory postsynaptic potentials (epsp) versus fiber volley amplitude (a measure of the number of presynaptic fibers activated). Appropriately, no significant difference should be observed between wt and mutant tissue for use in the assay.

While desirably, one may have wild-type hippocampal cells matched to the mutant cells, by having substantially no genetic difference affecting the assay, as a control, such control is not essential. By knowing the response of the wild-type cells to tetanic stimuli under the conditions of the assay, one can compare the results of the mutant cells with the known standard results. However, it will usually be desirable to have wild-type matched hippocampal cells to ensure that the observed results with the mutant have a direct comparison under the conditions of the assay. The control may be performed with and/or without the candidate drug to provide a comparison with the results from the mutant cells. In addition, one may have a comparison as to the effect of a known drug having a known activity on the mutant cells under the conditions of the assay. In this way one can directly compare the activity of the candidate drug to a known drug, as well as the activity of the candidate drug on wild-type cells in relation to the synaptic potential response to tetani. The assay is usually carried out over an extended period of time taking readings at different time points and determining the potentiation. Normally, the $GABA_A$ transmission by the cells will be intact.

The effect of tetanic stimulus on transmission is examined in the presence of intact $GABA_A$ receptor-mediated inhibition. In wt animals, a tetanus produces a moderate amount of potentiation. (FIG. 2a) In mutant animals, the potentiation following tetanus is greater than in wt animals. (FIG. 2a) Differences in potentiation between wt and mutant animals is statistically tested at various time points during a course of under 60 min post-tetanus and is found to be greater in mutants. LTP assessed in the presence of an NMDA receptor antagonist results in blocking potentiation in both the wt and mutant cells, showing that the mutant cells have enhanced potentiation and potentiation requires NMDA-receptor activation in both types of cells.

Blockade of the $GABA_A$ receptor also differentiates the response between mutant and wt cells. While $GABA_A$ receptor blockade increases LTP in wt animals, there is no significant increase in the mutant cells. It is concluded that the effect of the mutation on potentiation is occluded by blockade of inhibition, indicating that the two factors act on a common pathway.

In another test the effect of an agent on LTP with a moderately strong tetanus, e.g. three 1 second 100 Hz tetani), the potentiation is larger in mutant as compared to wt animals. However, with agents that increase $GABA_A$ receptor transmission, suppression of the enhanced potentiation should be observed. This can be demonstrated with flunitrazepam as a control or standard with which the effect of the candidate agent may be compared.

Finally, the ratio of peak inhibitory to excitatory responses is significantly greater in mutants as compared to wt. It appears that the observed result is relatively independent of the site of stimulation of the tissue and variations in stimulus intensity. Because of the greater ratio for mutant cells as compared to wt, depending upon the pathway and component of the pathway upon which the agents acts mutants may have a greater response to agents in the reduction of the difference in ratio between mutant and wt cells. This abnormality in mutants (increased inhibitory transmission) is indicated to be a homeostatic (feedback) system that has been turned on in these animals to suppress the underlying aberrant signaling (increased calcium rise). Candidate drugs may not directly affect the inhibitory transmission and still be efficacious, for example, if they act to suppress calcium rise through some other mechanism under the conditions of the assay.

Based on the tests described above, it appears that the presenilin in mutation and $GABA_A$ receptor transmission act on the same pathway that regulates potentiation of synaptic transmission. This can be explained by the mutation decreasing $GABA_A$ receptor transmission or the mutation acts downstream of $GABA_A$, receptor transmission, along the signal transduction pathway that generates potentiation. By measuring the effect of an agent on plasticity of mutant cells as compared to wt cells, one may influence the pathway associated with the $GABA_A$ receptor and restore the response toward the wt response.

It is evident from the above results that methods are provided employing mutated mammalian hippocampal cells, conveniently as tissue, which differ from wild-type cells in their increased potentiation as evidenced in their response to tetani. Furthermore, drugs can be screened to determine their effect on returning the response of the mutated cells to a wild-type response. Particularly, a mutation in presenilin protein, which enhances excitability of the cells upon stimuli, allows for screening of drugs which restore wild-type behavior, as demonstrated with a benzodiazepine. By employing tetani under conditions where plasticity of the cells can be determined, an efficient screening tool is provided for determining effectiveness of drugs for the treatment of Alzheimer's disease.

The references described throughout this specification are fully incorporated by reference. Having now fully described the invention, it will be apparent to one of ordinary skill in the art that many changes and modifications can be made thereto without departing from the spirit or scope of the invention as set forth herein.

What is claimed is:

1. An in vitro method for screening for candidate drugs for the treatment of Alzheimer's disease, said method comprising:

contacting slices of mouse hippocampal tissue containing cells, having a PS-1 Δ9 mutation and having enhanced synaptic potentiation upon stimulation as compared to wild-type hippocampal cells with a candidate drug;

subjecting said mutant hippocampal cells to tetanic stimulation; and determining the effect of said candidate drug on the synaptic potentiation of said mutant hippocampal cells;

wherein a reduction in the enhanced synaptic potentiation of the mutant hippocampal cells is indicative of activity of a candidate drug for the treatment of Alzheimer's disease.

2. An in vitro method for screening for candidate drugs for the treatment of Alzheimer's disease, said method comprising:

contacting mammalian hippocampal cells comprising a PS-1 Δ9 presenilin gene mutation wherein said hippocampal cells have enhanced synaptic potentiation upon stimulation as compared to wild-type hippocampal cells with a candidate drug;

subjecting said mutant hippocampal cells to tetanic stimulation; and determining the effect of said candidate drug on the synaptic potentiation of said mutant hippocampal cells;

wherein a reduction in the enhanced synaptic potentiation of the mutant hippocampal cells is indicative of activity of a candidate drug for the treatment of Alzheimer's disease.

3. The method according to claim 2, wherein mouse hippocampal tissue slices comprise said mutant hippocampal cells.

4. The method according to claim 2, wherein said enhanced synaptic potentiation is a result of a change in the $GABA_A$ receptor pathway.

5. An in vitro method for screening for candidate drugs for the treatment of Alzheimer's disease, said method comprising:

contacting mammalian hippocampal cells comprising a PS-1 Δ9 presenilin gene mutation and having enhanced synaptic potentiation upon stimulation as compared to wild-type hippocampal cells with a candidate drug;

subjecting said mutant hippocampal cells and said wild-type hippocampal cells to a tetanic stimulus;

measuring changes in potentiation with time of the mutant hippocampal cells and wild-type hippocampal cells and comparing the effect of said candidate drug on the synaptic potentiation of said mutant hippocampal cells as compared to the observed synaptic potentiation of said wild-type hippocampal cells;

wherein a reduction in the enhanced synaptic potentiation of the mutant hippocampal cells as compared to the synaptic potentiation of the wild-type cells is indicative of activity of a candidate drug for the treatment of Alzheimer's disease.

6. An in vitro method for screening for candidate drugs for the treatment of Alzheimer's disease, said method comprising:

contacting mammalian hippocampal cells comprising a PS-1 Δ9 presenilin gene mutation and having enhanced synaptic potentiation upon stimulation as compared to wild-type hippocampal cells with a candidate drug;

subjecting said mutant hippocampal cells and said wild-type hippocampal cells to a tetanic stimulus at a first potential of glutamate currents and a second potential of $GABA_A$ currents;

measuring the synaptic response at each of the first and second potentials for said mutant hippocampal cells and said wild-type hippocampal cells and comparing the effect of said candidate drug on said mutant hippocampal cells and said wild-type hippocampal cells;

wherein a reduction in the enhanced synaptic response of the mutant hippocampal cells without a significant change in the synaptic response of the wild-type cells is indicative of activity of a candidate drug for the treatment of Alzheimer's disease.

7. An in vitro method for screening for candidate drugs for the treatment of Alzheimer's disease, said method comprising:

contacting mouse hippocampal cells comprising a PS-1 Δ9 presenilin-1 gene mutation and having enhanced synaptic potentiation upon tetanic stimulation as compared to wild-type hippocampal cells, with a candidate drug;

subjecting said mutant hippocampal cells and said wild-type hippocampal cells to tetanic stimulation; and comparing the effect of said candidate drug on said mutant hippocampal cells and said wild-type hippocampal cells upon tetanic stimulation;

wherein a reduction in the enhanced synaptic potentiation of the mutant hippocampal cells without a significant change in the synaptic potentiation of the wild-type cells is indicative of activity of a candidate drug for the treatment of Alzheimer's disease.

8. A method for screening for a candidate drug that suppresses intracellular calcium rise in slices of mouse hippocampal tissue containing cells having a PS-1 Δ9 mutation in a presenilin gene combined with a candidate drug for the treatment of Alzheimer's disease, said method comprising:

contacting hippocampal cells comprising a presenilin gene mutation and having enhanced synaptic potentiation upon stimulation as compared to wild-type hippocampal cells with a candidate drug that suppresses intracellular calcium rise in said cells;

subjecting said mutant hippocampal cells to tetanic stimulation; and determining the effect of said candidate drug on the ratio of peak inhibitory to excitory responses;

wherein an enhanced said ratio of peak inhibitory to excitory responses in said mutant hippocampal cells as compared to wild-type hippocampal cells is indicative of activity of a candidate drug for the treatment of Alzheimer's disease.

* * * * *